US009101512B2

(12) United States Patent
Nakano

(10) Patent No.: US 9,101,512 B2
(45) Date of Patent: Aug. 11, 2015

(54) ABSORBENT-BODY MANUFACTURING APPARATUS

(75) Inventor: Takumi Nakano, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 497 days.

(21) Appl. No.: 13/636,803

(22) PCT Filed: Mar. 17, 2011

(86) PCT No.: PCT/JP2011/056371
§ 371 (c)(1),
(2), (4) Date: Nov. 21, 2012

(87) PCT Pub. No.: WO2011/118495
PCT Pub. Date: Sep. 29, 2011

(65) Prior Publication Data
US 2013/0059713 A1 Mar. 7, 2013

(30) Foreign Application Priority Data

Mar. 26, 2010 (JP) ................. 2010-072537

(51) Int. Cl.
B31B 1/00 (2006.01)
A61F 13/15 (2006.01)
(52) U.S. Cl.
CPC ..... A61F 13/15658 (2013.01); A61F 13/15707 (2013.01); A61F 13/15723 (2013.01); A61F 13/15772 (2013.01)
(58) Field of Classification Search
CPC ............ B31B 19/90; B31B 2219/9022; B65B 61/188; B65H 45/163; B65H 45/165; B65H 45/168; B65H 45/164; B41F 13/62
See application file for complete search history.

(56) References Cited

U.S. PATENT DOCUMENTS 5,057,064 A * 10/1991 Michalik ............................. 493/8
5,065,993 A * 11/1991 Reponty .......................... 270/49

(Continued)

FOREIGN PATENT DOCUMENTS

CN 1401302 A 3/2003
CN 1496725 A 5/2004

(Continued)

OTHER PUBLICATIONS

International Search Report for PCT/JP2011/056371, dated Jun. 14, 2011.

(Continued)

Primary Examiner — Sameh Tawfik
(74) Attorney, Agent, or Firm — Lowe Hauptman & Ham, LLP

(57) ABSTRACT

An absorbent-body manufacturing apparatus manufactures an absorbent body by depositing absorbent-body material in a plurality of recess sections spaced at an arrangement pitch on an outer circumferential face of a drum. The apparatus has a driving source that drives the drum in synchronization with another apparatus based on a synchronization signal. First and second signal-generating sections repeatedly generate first and second rotational-angle signals based on a rotation of the drum with a rotational angle of the drum as a unit, the rotational angle of the drum corresponding to first and second pitches, respectively. Depending on whether the arrangement pitch is set to the first or second pitch, a controller controls rotational driving operation of the driving source based on the first or second rotational-angle signal and on the synchronization signal.

7 Claims, 8 Drawing Sheets

(56) References Cited

U.S. PATENT DOCUMENTS

| | | | |
|---|---|---|---|
| 5,088,708 A * | 2/1992 | Nowak | 270/47 |
| 5,359,525 A * | 10/1994 | Weyenberg | 700/124 |
| 5,659,538 A * | 8/1997 | Stuebe et al. | 700/124 |
| 6,761,678 B1 * | 7/2004 | Miescher et al. | 493/434 |
| 7,083,561 B2 * | 8/2006 | Prum | 493/424 |
| 7,172,666 B2 * | 2/2007 | Groves et al. | 156/64 |
| 7,435,210 B2 * | 10/2008 | Leupold et al. | 493/424 |
| 8,062,459 B2 * | 11/2011 | Nakakado et al. | 156/256 |
| 8,221,572 B2 * | 7/2012 | Yamamoto | 156/176 |
| 2002/0019301 A1* | 2/2002 | Hachiya et al. | 493/356 |
| 2003/0047273 A1 | 3/2003 | Kojo et al. | |
| 2004/0123954 A1 | 7/2004 | Yoneoka et al. | |

FOREIGN PATENT DOCUMENTS

| | | |
|---|---|---|
| CN | 101663007 A | 3/2010 |
| JP | 2004155586 A | 6/2004 |
| JP | 2007054219 A | 3/2007 |
| JP | 2007167509 A | 7/2007 |
| JP | 2007260414 A | 10/2007 |
| JP | 2008154964 A | 7/2008 |

OTHER PUBLICATIONS

Extended European Search Report issued Apr. 11, 2014, corresponds to European patent application No. 11759301.2.

Office Action mailed Jan. 26, 2014, corresponds to Chinese patent application No. 201180016014.7.

* cited by examiner

ABSORBENT-BODY MANUFACTURING APPARATUS

RELATED APPLICATIONS

The present application is a National Phase of International Application Number PCT/JP2011/056371, filed Mar. 17, 2011, and claims priority from Japanese Application Number 2010-072537, filed Mar. 26, 2010.

TECHNICAL FIELD

The present invention relates to an apparatus for manufacturing an absorbent body of an absorbent article such as a sanitary napkin.

BACKGROUND ART

Conventionally, sanitary napkins and the like are known as absorbent articles that absorb fluid such as excreted fluid. These absorbent articles include, as a constituent component, an absorbent body that absorbs fluid. The absorbent body has a base material obtained by molding an absorbent-body material such as a pulp fiber into a predetermined shape.

Such an absorbent body is manufactured by a fiber depositing apparatus. The fiber depositing apparatus has a rotating drum that is driven to rotate. On an outer circumferential face of the rotating drum, recess molds are intermittently arranged at a predetermined arrangement pitch in the rotating direction. Then, absorbent bodies are produced by supplying the absorbent-body material from an appropriate duct toward the molds on the outer circumferential face of the rotating drum and depositing the absorbent-body material in the molds ([PTL 1]).

CITATION LIST

Patent Literature

[PTL 1] JP 2007-54219A

SUMMARY OF INVENTION

Technical Problem

This sort of fiber depositing apparatus is driven to rotate in synchronization with apparatuses other than the fiber depositing apparatus in order to manufacture napkins in cooperation with the other apparatuses, the other apparatuses being positioned upstream or downstream from the fiber depositing apparatus.

Here, synchronization with such another apparatus is achieved as follows. First, a synchronization signal is a signal indicating a rotational angle of 0° to 360°, for example. The synchronization signal is repeatedly output, and this rotational angle of 0° to 360° is allocated to a unit amount of motion of the other apparatus, a unit amount of motion corresponding to a production pitch. On the other hand, the rotating drum is provided with an encoder, and an input shaft of the encoder rotates once while the rotating drum rotates by a rotational angle corresponding to an arrangement pitch of the molds. Thus, when the rotating drum rotates by an amount corresponding to the arrangement pitch, the encoder outputs a signal indicating a rotational angle of 0° to 360°. An appropriate controller controls rotational driving of the rotating drum such that a rotational-angle indication value from this encoder matches a rotational-angle indication value of the synchronization signal. Therefore, the synchronization operation with the other apparatus is realized.

Adjustment for associating one rotation of the input shaft of the encoder with a rotational motion (rotational angle) of the rotating drum corresponding to the arrangement pitch is performed using a rotational-movement transmission mechanism that transmits the rotational motion of the rotating drum to the input shaft of the encoder. The rotational-movement transmission mechanism includes: a first pulley that is disposed on the rotational shaft of the rotating drum; a second pulley that is disposed on the input shaft of the encoder; and an endless belt that is wrapped around the first pulley and the second pulley, for example. Thus, the foregoing adjustment is performed by appropriately setting a rotation ratio, which is a ratio between the diameter of the pitch circle of the first pulley and the diameter of the pitch circle of the second pulley. In the following description, the diameter of the pitch circle of a pulley may be simply referred to as the diameter of the pulley.

In the production line, the size of napkins that are to be produced is changed periodically. At that time, change in product size is performed also in the fiber depositing apparatus. For example, at the time of change in product size from M to L in the fiber depositing apparatus, a plurality of arc-shaped mold plates which form the outer circumferential face are first detached from the cylindrical drum main body which forms the core of the rotating drum. It should be noted that the molds are included on the mold plates. In their place, mold plates for the L size are attached to the drum main body. Consequently, the change in product size in the rotating drum ends.

Since the mold arrangement pitch has been changed to that for the L size, the encoder has to be reset for the L size. That is to say, at this time, the input shaft of the encoder rotates once during a period when the rotating drum rotates by a rotational angle corresponding to an arrangement pitch for the M size. Therefore, the setting has to be changed such that the input shaft of the encoder rotates once during a period when the rotating drum rotates by the rotational angle corresponding to an arrangement pitch for the L size.

This change is made by changing the rotation ratio of the input shaft of the encoder to the rotational shaft of the rotating drum. For example, the second pulley having the diameter for the M size is detached from the input shaft of the encoder and replaced by a second pulley having the diameter for the L size.

However, at the time of the replacement operation, the input shaft of the encoder rotates idly and rotates relatively to the rotating drum, for example. As a result, the rotational-angle indication value indicated by the encoder and the rotational position of the rotating drum no longer correspond to each other. This causes error in synchronization between the fiber depositing apparatus and the other apparatus. Therefore, the positional relationship between the indication value from the encoder and the rotational position of the rotating drum has to be re-adjusted, which requires a great amount of effort.

The invention has been made in view of such a conventional problem, and an advantage thereof is to reduce work load for change in product size in an absorbent-body manufacturing apparatus.

Solution to Problem

In order to achieve the above-described advantage, a primary aspect of the invention is directed to an absorbent-body manufacturing apparatus that has a driving source that drives a drum to rotate about a rotational shaft in synchronization with another apparatus based on a synchronization signal, the synchronization signal being repeatedly output taking a unit amount of motion of the other apparatus as a unit, the unit amount of motion corresponding to a production pitch, that manufactures an absorbent body by supplying an absorbent-body material and depositing the absorbent-body material in a plurality of recess sections, the supplying being performed from a duct toward the plurality of recess sections, the plurality of recess sections being spaced at a predetermined arrangement pitch in a rotating direction on an outer circumferential face of the drum, the duct being disposed at a predetermined position in the rotating direction, comprising:

a first-pitch positioning member for setting the arrangement pitch to a first pitch;

a second-pitch positioning member for setting the arrangement pitch to a second pitch that is different from the first pitch;

a first signal-generating section that repeatedly generates a first rotational-angle signal based on a rotation of the drum taking a rotational angle of the drum as a unit, the rotational angle of the drum corresponding to the first pitch;

a second signal-generating section that repeatedly generates a second rotational-angle signal based on a rotation of the drum taking a rotational angle of the drum as a unit, the rotational angle of the drum corresponding to the second pitch; and a controller that controls rotational driving of the driving source, wherein in the case where the arrangement pitch is set to the first pitch, the controller controls rotational driving of the driving source based on the first rotational-angle signal and the synchronization signal, and in the case where the arrangement pitch is set to the second pitch, the controller controls rotational driving of the driving source based on the second rotational-angle signal and the synchronization signal.

Features of the invention other than the above will become clear by reading the description of the present specification with reference to the accompanying drawings.

Advantageous Effects of Invention

The invention reduces work load for change in product size in an absorbent-body manufacturing apparatus.

DESCRIPTION OF EMBODIMENTS

Figure 1:
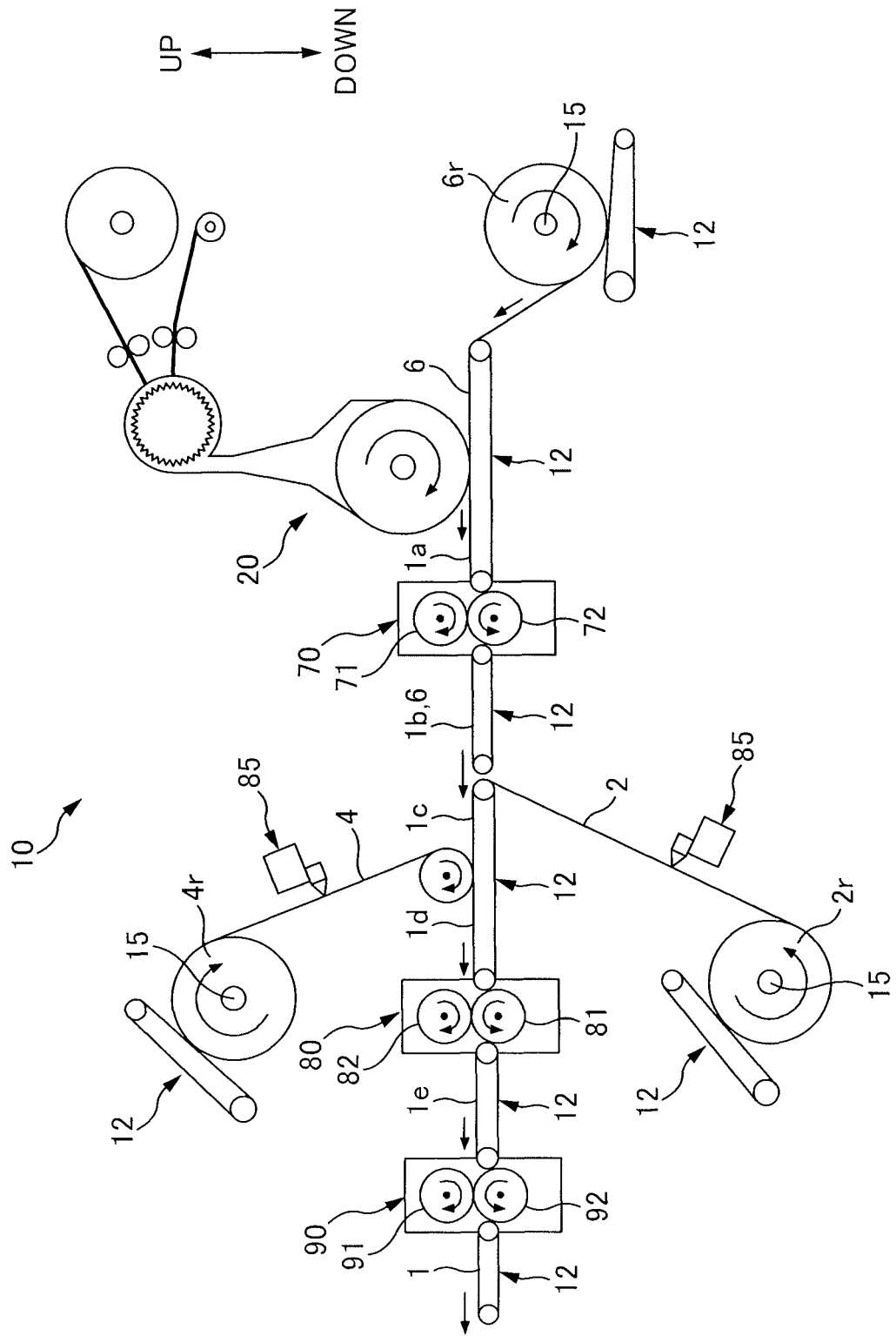
FIG. 1 is a schematic side view of a production line 10 of napkins 1.

At least the following matters will be made clear by the explanation in the present specification and the description of the accompanying drawings.

An absorbent-body manufacturing apparatus that has a driving source that drives a drum to rotate about a rotational shaft in synchronization with another apparatus based on a synchronization signal, the synchronization signal being repeatedly output taking a unit amount of motion of the other apparatus as a unit, the unit amount of motion corresponding to a production pitch, that manufactures an absorbent body by supplying an absorbent-body material and depositing the absorbent-body material in a plurality of recess sections, the supplying being performed from a duct toward the plurality of recess sections, the plurality of recess sections being spaced at a predetermined arrangement pitch in a rotating direction on an outer circumferential face of the drum, the duct being disposed at a predetermined position in the rotating direction, including:

a first-pitch positioning member for setting the arrangement pitch to a first pitch;

a second-pitch positioning member for setting the arrangement pitch to a second pitch that is different from the first pitch;

a first signal-generating section that repeatedly generates a first rotational-angle signal based on a rotation of the drum taking a rotational angle of the drum as a unit, the rotational angle of the drum corresponding to the first pitch;

a second signal-generating section that repeatedly generates a second rotational-angle signal based on a rotation of the drum taking a rotational angle of the drum as a unit, the rotational angle of the drum corresponding to the second pitch; and a controller that controls rotational driving of the driving source, wherein in the case where the arrangement pitch is set to the first pitch, the controller controls rotational driving of the driving source based on the first rotational-angle signal and the synchronization signal, and in the case where the arrangement pitch is set to the second pitch, the controller controls rotational driving of the driving source based on the second rotational-angle signal and the synchronization signal.

This absorbent-body manufacturing apparatus includes: a first signal-generating section used when the arrangement pitch of the recess sections is set to the first pitch; and a second signal-generating section used when the arrangement pitch is set to the second pitch. Thus, at the time of change in product size, in which the arrangement pitch changes to the first pitch or to the second pitch, it is unnecessary to reset the first signal-generating section and the second signal-generating section. This can reduce work load for the change in product size.

Furthermore, when the arrangement pitch is set to the first pitch, the controller can synchronize the rotational driving of the driving source with the other apparatus by associating the first rotational-angle signal with the synchronization signal. When the arrangement pitch is set to the second pitch, the controller can synchronize the rotational driving of the driving source with the other apparatus by associating the second rotational-angle signal with the synchronization signal. Thus, the rotational motion of the drum can be synchronized with the other apparatus both in the case of the first pitch and the case of the second pitch.

In this absorbent-body manufacturing apparatus, it is desirable that the first rotational-angle signal and the second rotational-angle signal are signals each having the same specification as the synchronization signal.

According to this absorbent-body manufacturing apparatus, both the first rotational-angle signal and the second rotational-angle signal are signals having the same specification as the synchronization signal. This makes it possible to easily associate each of the rotational-angle signals with the synchronization signal in order to synchronize the rotation of the drum with the other apparatus.

In this absorbent-body manufacturing apparatus, it is desirable that the first rotational-angle signal is a signal indicating a phase of 0° to 360°, the second rotational-angle signal is a signal indicating a phase of 0° to 360°, and the synchronization signal is a signal indicating a phase of 0° to 360°.

According to this absorbent-body manufacturing apparatus, all of the first rotational-angle signal, the second rotational-angle signal, and the synchronization signal are signals each indicating a phase of 0° to 360°. This makes it possible to easily associate each of the rotational-angle signals with the synchronization signal in order to synchronize the rotation of the drum with the other apparatus.

In this absorbent-body manufacturing apparatus, it is desirable that the first signal-generating section and the second signal-generating section are signal-generating sections having the same specification, the first signal-generating section has a first input shaft, and generates the first rotational-angle signal by rotation of the first input shaft, the second signal-generating section has a second input shaft, and generates the second rotational-angle signal by rotation of the second input shaft, the rotational shaft of the drum integrally rotates with the drum, a rotational motion of the drum is input from the rotational shaft to the first input shaft and the second input shaft via a rotational-movement transmission mechanism, and when the number of the recess sections arranged at the first pitch PM on the drum is NM, and the number of the recess sections arranged at the second pitch PL on the drum is NL, the rotational-movement transmission mechanism is set such that a rotation ratio RM of the first input shaft to the rotational shaft is NM and such that a rotation ratio RL of the second input shaft to the rotational shaft is NL.

According to this absorbent-body manufacturing apparatus, signal-generating sections having the same specification are used as the first signal-generating section and the second signal-generating section. Thus, when synchronizing the rotational motion of the drum with the motion of the other apparatus, the signal-generating sections can be reliably associated with the synchronization signal.

Furthermore, because of the foregoing relationships of the rotation ratios, change in product size between the first pitch PM and the second pitch PL can be performed without causing any problem.

In this absorbent-body manufacturing apparatus, it is desirable that the rotational-movement transmission mechanism has at least one relay shaft, the rotational motion of the drum is transmitted from the rotational shaft to the first input shaft and the second input shaft via the relay shaft, the rotation ratio RM is divided by the relay shaft into a plurality of rotation ratios that are each smaller than the rotation ratio RM, and the rotation ratio RL is divided by the relay shaft into a plurality of rotation ratios that are each smaller than the rotation ratio RL.

According to this absorbent-body manufacturing apparatus, since a relay shaft is used, the degree of freedom in the arrangement positions of the first and the second signal-generating sections can be increased.

Furthermore, each of the rotation ratios RM and RL of the rotational motion transmitted from the rotational shaft to the first and second input shafts is divided by the relay shaft into smaller rotation ratios. This makes it possible to precisely transmit the rotational motion of the drum to the first and second input shafts. A detailed description thereof will be given later.

In this absorbent-body manufacturing apparatus, it is desirable that in order to transmit the rotational motion of the drum to the first input shaft and the second input shaft, the rotational shaft is coupled to the rotational-movement transmission mechanism at a predetermined portion on the rotational shaft, and the predetermined portion is commonly applied to both the case where the arrangement pitch is the first pitch and the case where the arrangement pitch is the second pitch.

According to this absorbent-body manufacturing apparatus, the predetermined portion on the rotational shaft is commonly applied both to the first pitch and the second pitch. Thus, at the time of change in product size, it is unnecessary to handle the rotational-movement transmission mechanism. This can reduce work load required for the change in product size.

In this absorbent-body manufacturing apparatus, it is desirable that an ejection opening of the duct for ejecting and supplying the absorbent-body material is disposed opposite the outer circumferential face of the drum, and a diameter of the drum formed by the first-pitch positioning member is equal to a diameter of the drum formed by the second-pitch positioning member.

According to this absorbent-body manufacturing apparatus, the diameter of the drum whose arrangement pitch is the first pitch is equal to the diameter of the drum whose arrangement pitch is the second pitch. Therefore, it is unnecessary to replace the duct for ejecting and supplying the absorbent-body material; that is, the duct can be commonly used. This can reduce work load for the change in product size.

Embodiment

<<<Schematic Configuration of Production Line 10>>>

FIG. 1 is a schematic side view of a production line 10 of absorbent articles 1. The production line 10 produces sanitary napkins 1 as an example of the absorbent articles 1 that absorb excreted fluid.

Figure 2A:
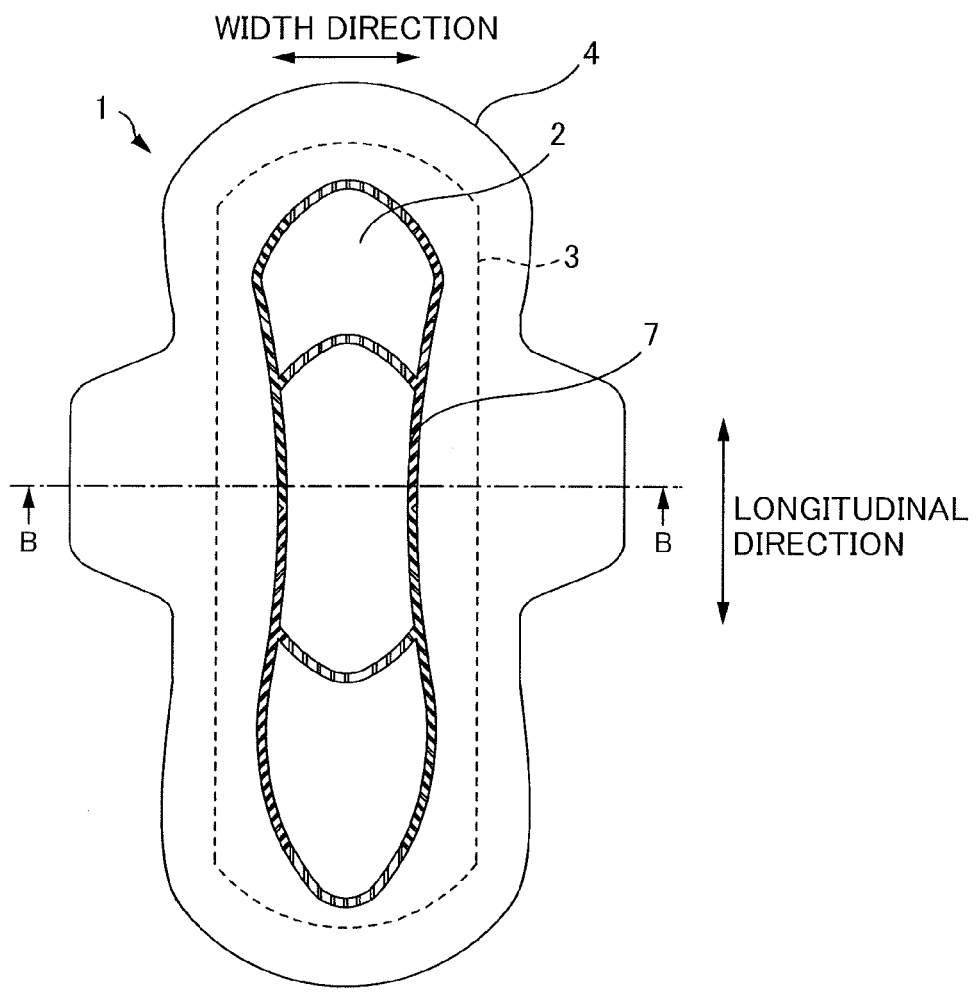
FIG. 2A is a plan view of the napkin 1.
Figure 2B:
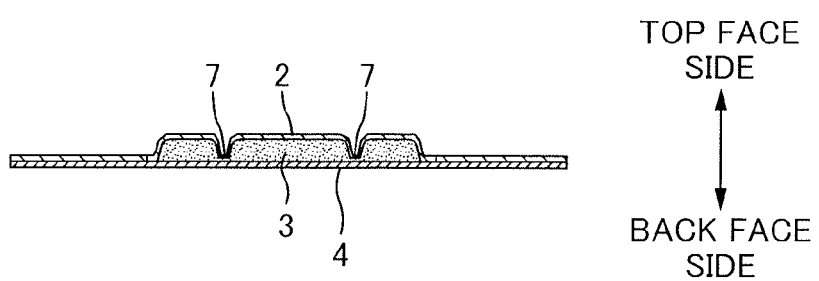
FIG. 2B is a cross-sectional view taken along B-B in FIG. 2A.

FIG. 2A is a plan view of the napkin 1, and FIG. 2B is a cross-sectional view taken along B-B in FIG. 2A.

In the napkin 1, for example, an absorbent body 3 and a carrier sheet (not shown in FIGS. 2A and 2B) are interposed together between a fluid-permeable top sheet 2 such as non-woven fabric and a fluid-impermeable back sheet 4 such as a film. The absorbent body 3 is mainly made of a pulp fiber 5 and the carrier sheet 6 is made of materials such as tissue paper.

Note that an embossed groove 7 is formed by embossing or the like on substantially the central area of the napkin 1 in the longitudinal direction and the width direction. Thus, the constituent components 2, 3, 4, and 6 forming the napkin 1 are integrated.

As shown in FIG. 1, the production line 10 for the napkins 1 has a plurality of transport mechanisms 12 that transport semi-finished products 1a, 1b, ... of the napkins 1 in the transport direction. As the transport mechanisms 12, suction belt conveyors 12 whose placement faces have a suction function are used, and are respectively driven by driving sources each configured by a motor (not shown). Note that, in some cases, transport rollers may be used.

While the semi-finished products 1a, 1b, ... are transported by the transport mechanisms 12 in the transport direction, the semi-finished products 1a, 1b, ... are sequentially subjected to various processes such as pressing, punching, application of a hot melt adhesive (hereinafter, also referred to as an "HMA"), joining with other parts, and the like; thereby, the napkins 1 are completely formed. In the following description, a direction orthogonal to the transport direction (the direction that passes through the section of the diagram in FIG. 1) is also referred to as a "CD direction".

As shown in FIG. 1, the production line 10 has a plurality of reels 15. The reels 15 are arranged, for example, respectively on the top sheet 2, the back sheet 4, and the carrier sheet 6. All of the sheets 2, 4, and 6 are introduced to the production line 10 in the form of sheet rolls formed by spooling the sheets. Sheet rolls 2r, 4r, and 6r are respectively attached to the corresponding reels 15 and unwound in the form of continuous sheets from the reels.

Furthermore, the production line 10 has, as typical processing apparatuses, a fiber depositing apparatus 20, an absorbent-body rotary cutter 70, an embossment pressing apparatus 80, a rotary die cutter apparatus 90, and the like, and further has HMA application apparatuses 85 at a plurality of positions along the transport direction.

The fiber depositing apparatus 20 forms the absorbent bodies 3 (FIG. 3) by molding the pulp fiber 5, which is an example of the absorbent-body material, into a predetermined, substantially rectangular solid shape. And, the fiber depositing apparatus 20 places the formed absorbent bodies 3 on the carrier sheet 6 at a production pitch P in the transport direction.

The absorbent-body rotary cutter 70 is disposed downstream of the fiber depositing apparatus 20. The rotary cutter 70 has a cutter roll 71 and an anvil roll 72 that are driven to rotate at positions opposite each other. When the carrier sheet 6 having the absorbent bodies 3 thereon passes through the nip between the rolls 71 and 72, the carrier sheet 6 is cut at positions between the absorbent bodies 3 (FIG. 3); the carrier sheet 6 having the absorbent bodies 3 thereon at this point is the semi-finished product 1a. Accordingly, the semi-finished products 1b are formed.

Downstream of the rotary cutter 70, the position where the semi-finished products 1b merge with the top sheet 2 is located. That is to say, at this position, the top sheet 2 is supplied and attached to the carrier sheet 6 of the semi-finished product 1b so as to cover the carrier sheet 6 from below. Here, at a point before the merging position on the supply route of the top sheet 2, a hot melt adhesive is applied in advance to the top sheet 2 by the HMA application apparatus 85 as preparation for the attaching.

To the downstream of the above-described merging position, located is the position where the semi-finished products 1c merge with the back sheet 4. Thus, at this position, the semi-finished product 1c includes the carrier sheet 6, the absorbent body 3, and the top sheet 2; the carrier sheet 6 and the absorbent body 3 are successively placed on the top sheet 2. The back sheet 4 is supplied and attached from above to the semi-finished product 1c so as to cover the semi-finished product 1c from above. Here, at a point before the merging position on the supply route of the back sheet 4, a hot melt adhesive is applied in advance to the back sheet 4 by the HMA application apparatus 85 as preparation for the attaching.

Subsequently, the semi-finished product 1d is transported to the embossment pressing apparatus 80. The embossment pressing apparatus 80 has an embossing roll 81 and an anvil roll 82 that are driven to rotate at positions opposite each other. The embossing roll 81 has a projecting section in the shape corresponding to the embossed groove 7 (FIG. 2). Thus, when the semi-finished product 1d passes through a nip between the rolls 81 and 82, the semi-finished product 1d is embossed by the projecting section, and, therefore, the embossed groove 7 is formed.

Finally the semi-finished product leis transported to the rotary die cutter apparatus 90. The apparatus 90 has a cutter roll 91 and an anvil roll 92 that are driven to rotate at positions opposite each other. When the semi-finished product 1d passes through a nip between the rolls 91 and 92, the semi-finished product 1d is punched out between the rolls 91 and 92 into the shape of the product of the napkin 1. Consequently, the sanitary napkin 1 is completed.

<<<Schematic Configuration of Fiber Depositing Apparatus 20>>>

Figure 3:
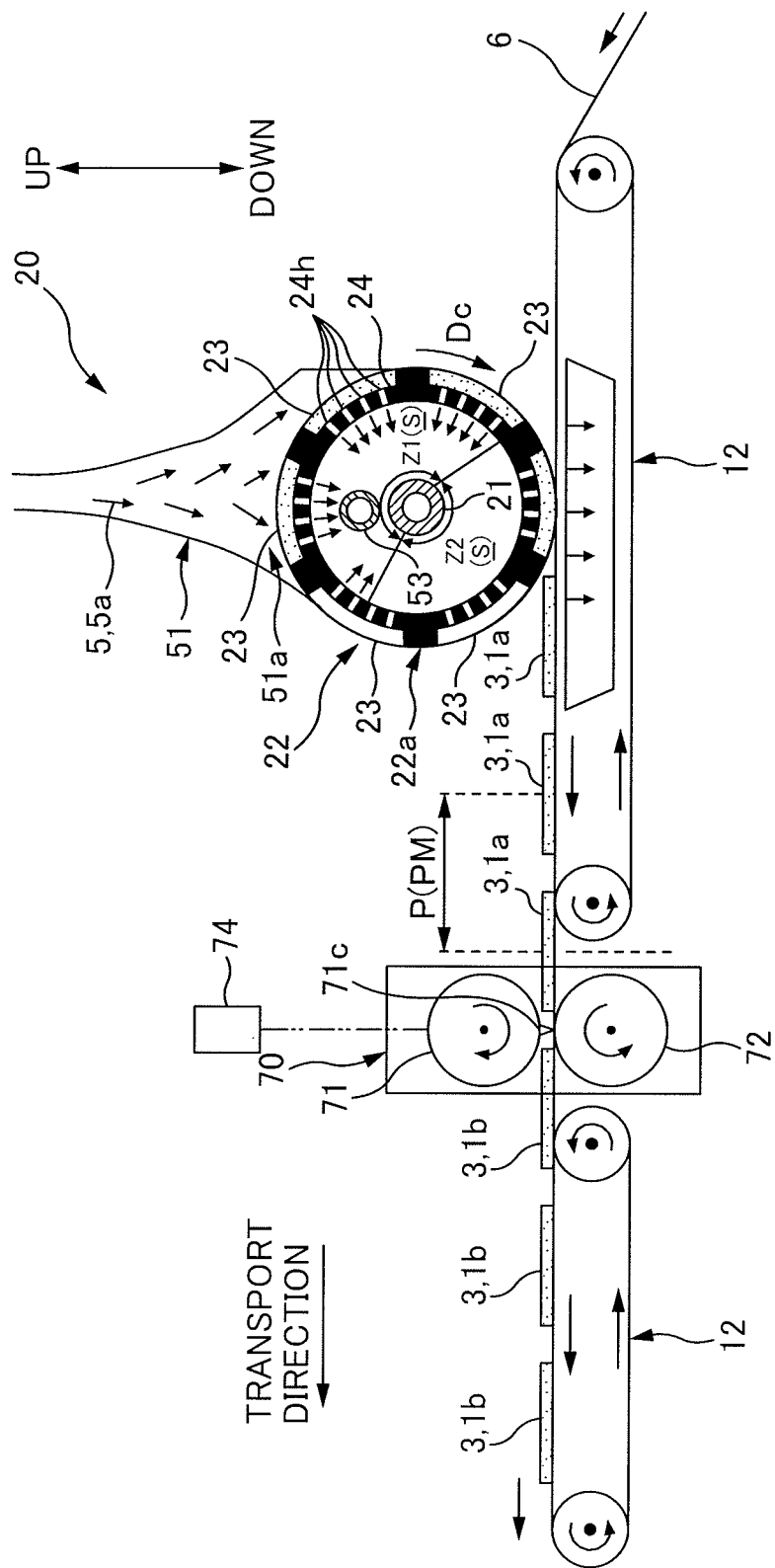
FIG. 3 is a central cross-sectional view of a fiber depositing apparatus 20, which is a manufacturing apparatus 20 for absorbent bodies 3.

FIG. 3 is a central cross-sectional view of the fiber depositing apparatus 20, which is a manufacturing apparatus 20 for the absorbent bodies 3. Note that FIG. 3 shows part of the configuration viewed from a side.

The fiber depositing apparatus 20 includes: a rotating drum 22 (corresponding to a "drum") that continuously rotates about a rotational shaft 21 in one direction (e.g., in a clockwise direction) of a rotating direction Dc, the rotational shaft 21 being along the CD direction; and a scattering duct 51 (corresponding to a "duct") that ejects mixed air 5a containing the pulp fiber 5 toward an outer circumferential face 22a of the rotating drum 22 from a scattering opening 51a (corresponding to an "ejection opening"), the scattering opening 51a being disposed at a predetermined position in the rotating direction Dc, for example.

The rotating drum 22 is substantially cylindrical in shape. And, on its outer circumferential face 22a, the rotating drum 22 has recess-shaped molds 23 (corresponding to "recess sections") whose shape corresponds to the absorbent body 3 that is to be molded and which are intermittently arranged at the predetermined arrangement pitch P in the rotating direction Dc. As the bottom face of each mold 23, an air permeable member 24 is arranged. The internal portion of the mold 23 communicates with the internal portion of the rotating drum 22 through air holes 24h of the air permeable members 24 in an air-permeable manner.

Inside the rotating drum 22, a substantially closed space S having a doughnut-shape is formed between the inner circumferential face and the rotational shaft 21. The substantially closed space S is divided into zones along the rotating direction Dc by a plurality of partitions (not shown). Through suction from a suction duct 53, a first zone Z1 is kept at a negative pressure that is lower than the outside pressure. A second zone Z2, which is on the downstream side of the first zone Z1, is kept at a pressure that is the same as or slightly higher than the outside pressure. The scattering opening 51a of the scattering duct 51 is disposed corresponding to the first zone Z1. The suction belt conveyor 12, which is the transport mechanism 12 described above, is disposed corresponding to the second zone Z2.

Thus, according to the fiber depositing apparatus 20, the absorbent body 3 is molded as follow. The mold 23 is passing through a position below the scattering duct 51 by the rotation of the rotating drum 22. The mixed air 5a is ejected from the scattering opening 51a and substantially only the air component thereof is sucked into the air permeable member 24 on the bottom face of the mold 23. Therefore, the pulp fibers 5 contained in the mixed air 5a are deposited on the air permeable member 24. When the mold 23 has passed through the position below the scattering opening 51a and reaches a position opposite the suction belt conveyor 12, the pulp fiber 5 in the mold 23 is sucked outward through suction from the suction belt conveyor 12 and released one by one from the mold 23, and is then transported as the absorbent body 3 by the suction belt conveyor 12.

Incidentally, it is possible that a polymer injection pipe (not shown) is provided in the scattering duct 51 to discharge superabsorbent polymer from an opening of the polymer injection pipe towards the rotating drum 22.

<<<Configuration of Rotating Drum 22>>>

Figure 4:
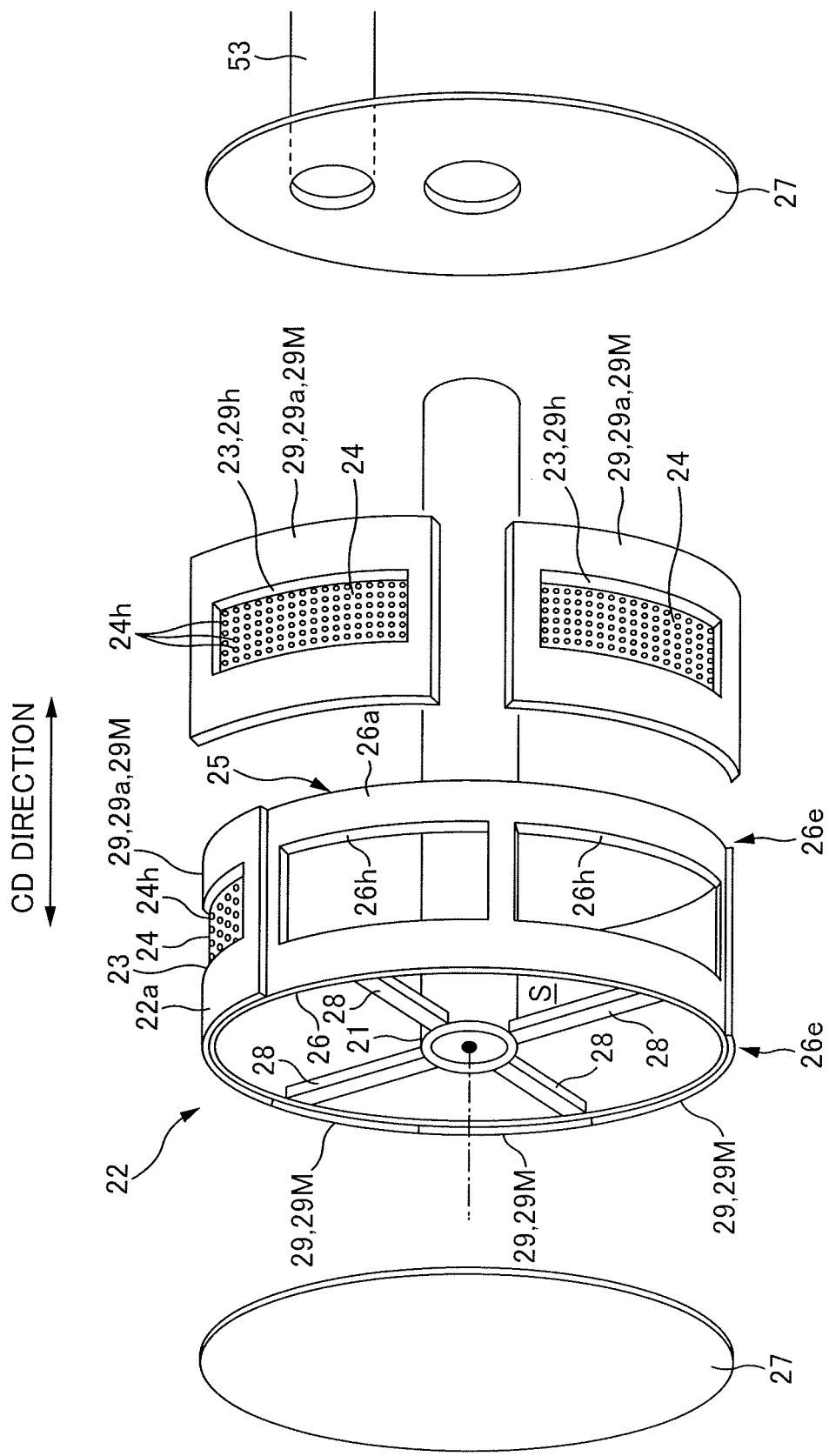
FIG. 4 is an exploded perspective view of a rotating drum 22.
Figure 5:
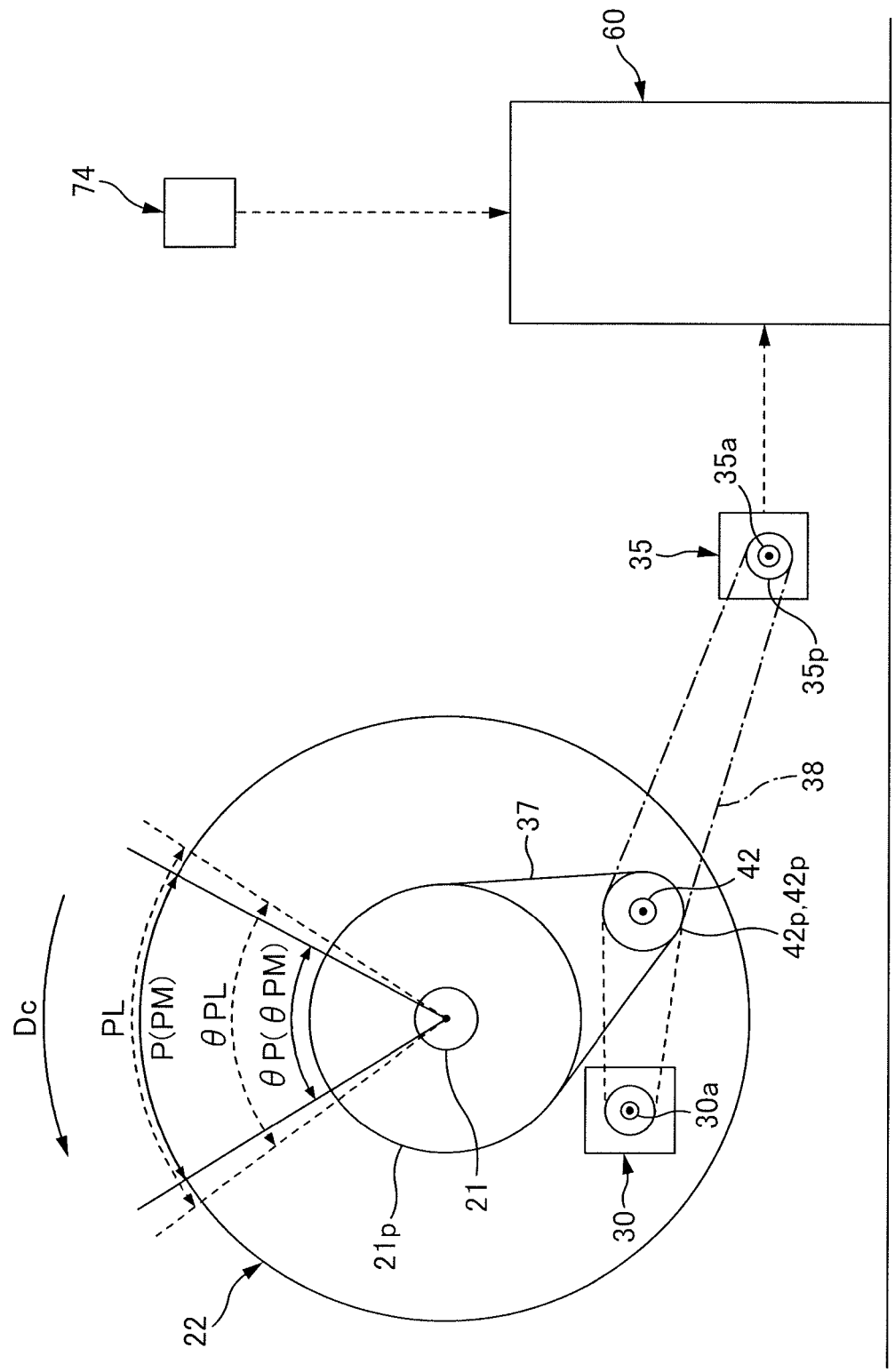
FIG. 5 is a schematic side view of the rotating drum 22 according to a reference example viewed from the side of a driving mechanism.

FIG. 4 is an exploded perspective view of the rotating drum 22. Furthermore, FIG. 5 is a schematic side view of the rotating drum 22 according to a reference example viewed from the side of a driving mechanism.

As shown in FIG. 4, the rotating drum 22 has a drum main body 25 and a plurality of mold plates 29 that are attached to the outer circumferential face of the drum main body 25 in a detachable manner.

The drum main body 25 has a cylindrical section 26 and the rotational shaft 21. The cylindrical section 26 and the rotational shaft 21 are coaxially arranged and are integrally coupled to each other with a plurality of spoke-like members 28. On one end of the rotational shaft 21, a bearing member (not shown) is disposed. Through this bearing member, the drum main body 25 is rotatably supported on a base (not shown) of the fiber depositing apparatus 20. A rotational driving force is input from a motor 30 (described later) to the rotational shaft 21, and, therefore, the rotating drum 22 is driven to rotate. Meanwhile, on the cylindrical section 26, opening sections 26h are formed at portions where the molds 23 are to be positioned, and the opening sections 26h are slightly larger than the molds 23. Furthermore, two end edges 26e in the CD direction of the cylindrical section 26 are respectively closed by circular fixing walls 27. Accordingly, the above-described substantially closed space S is formed inside the cylindrical section 26.

Concerning the mold plates 29, the main body thereof is, for example, an arc-shaped plate 29a having a length obtained by equally dividing the circumferential length of the outer circumferential face 22a of the rotating drum 22 by the number (six in FIG. 4) of molds 23 that are to be arranged. At the planar center of the arc-shaped plate 29a, an opening section 29h is formed whose shape corresponds to a shape in which the absorbent body 3 is to be molded. The opening section 29h is covered by the air permeable member 24 from the inner circumferential face side of the arc-shaped plate 29a, and this air permeable member 24 forms the bottom face of the mold 23 on which the pulp fiber 5 is to be deposited. In this example, one opening section 29h forming the mold 23 is provided on each mold plate 29. However, the invention is not limited thereto. For example, two or more opening sections 29h may be provided on each mold plate 29.

Such mold plates 29 are sequentially attached by means such as bolting to predetermined positions on an outer circumferential face 26a of the cylindrical section 26; when attaching the plates, benchmarks that are arranged in advance on the cylindrical section 26 of the drum main body 25 are used as reference points. Such benchmarks are arranged for each size such as an M size or an L size in order to support size change, which will be described later. Concerning the mold plate 29, there are provided a mold plate 29M (corresponding to a "first-pitch positioning member") for the M size and a mold plate 29L (corresponding to a "second-pitch positioning member") for the L size. If the mold plates 29 are attached based on the benchmarks, basically, the positional relationship necessary for synchronization with the cutter roll 71 (described later) is ensured regardless of whether the size is the M size or the L size. FIG. 4 shows the mold plates 29M for the M size.

As shown in FIG. 5, the rotating drum 22 is driven to rotate by a driving source configured by the motor 30. In order to synchronize this rotational driving with an apparatus other than the rotating drum 22 such as the rotary cutter 70 on the production line 10, a rotary encoder 35 that detects the rotational angle of the rotating drum 22 is disposed. In this reference example, the rotating drum 22 is set so as to rotate in synchronization with the above-described cutting operation by the absorbent-body rotary cutter 70.

Specifically, as shown in FIG. 3, the cutter roll 71 of the absorbent-body rotary cutter 70 has only one flat blade 71c on an outer circumferential face 71a; the flat blade 71c is arranged on a part of the circumference and extends along the CD direction. Furthermore, the cutter roll 71 is controlled so as to rotate once during a period in which one of the semi-finished products 1a arranged at the production pitch P in the transport direction is transported through the apparatus 70. At this state, the semi-finished product 1a is the carrier sheet 6 on which the absorbent bodies 3 are placed; therefore, this carrier sheet 6 having the absorbent bodies 3 thereon is divided by the production pitch P at a position between the absorbent bodies 3. Further, the cutter roll 71 includes a rotary encoder 74 which detects the rotational angle of the cutter roll 71 and outputs a detection signal. For example, one rotation of the cutter roll 71 is the unit amount of motion of the cutter roll 71, the signal which indicates a phase of 0° to 360° is repeatedly output taking one rotation of the cutter roll 71 as a unit, the phase being proportional to the rotational angle of the cutter roll 71. Then, this detection signal serves as a synchronization signal and is transmitted to a controller 60 that controls rotational driving of the rotating drum 22.

Here, as shown in FIG. 3, an input shaft 35a of the encoder 35 of the rotating drum 22 according to this reference example is set so as to rotate once during a period in which the rotating drum 22 rotates by a rotational angle θP corresponding to the arrangement pitch P of the molds 23; the arrangement pitch P is the production pitch P. Therefore, during a period of one rotation, signals indicating a phase of 0° to 360° are output so that the phase of the signals is in proportion to the rotational angle of the input shaft 35a. Based on the above-described synchronization signal and the rotational-angle signal from the encoder 35 of the rotating drum 22, the controller 60 controls rotational driving of the motor 30 of the rotating drum 22. That is to say, the controller 60 outputs a drive current I to the motor 30 while performing control such that a difference Δθ between a rotational-angle indication value θa indicated by the synchronization signal and a rotational-angle indication value θr indicated by the detection signal is reduced.

Figure 6:
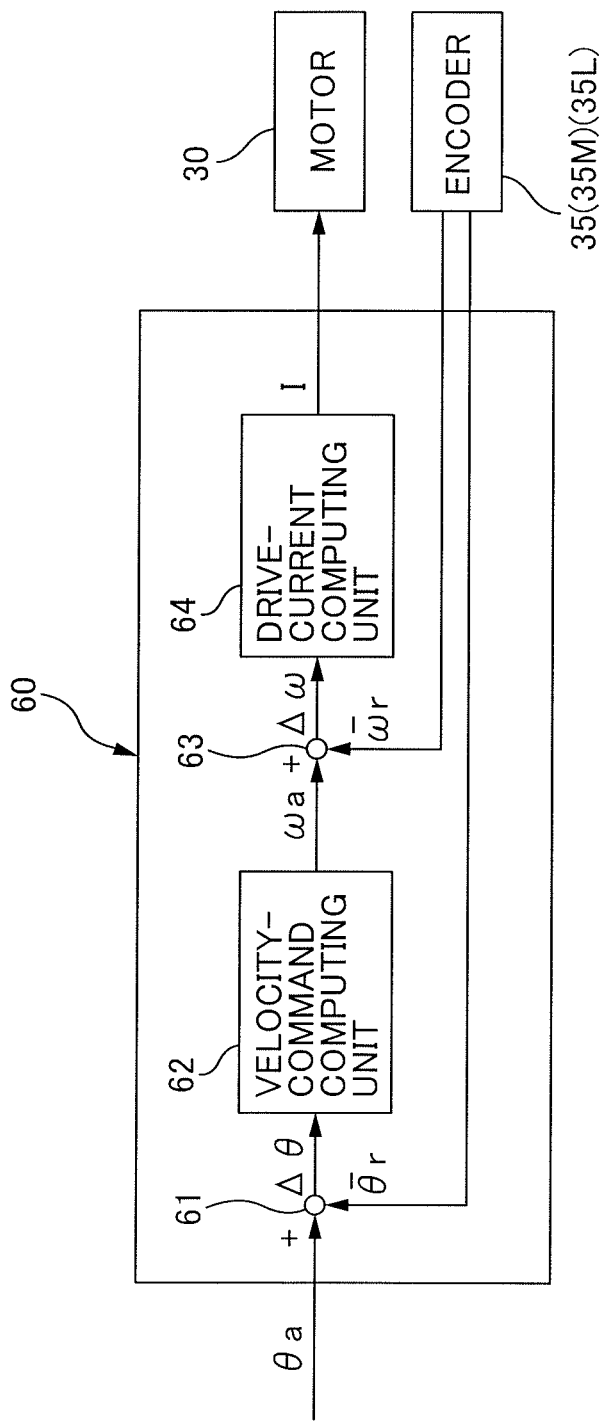
FIG. 6 is a schematic configuration diagram of a controller 60.

FIG. 6 is a schematic configuration diagram of the controller 60. In this example, the control is performed regarding the position. Specifically, the controller 60 has a position comparing unit 61, a velocity-command computing unit 62, a velocity comparing unit 63, and a drive-current computing unit 64. The position comparing unit 61 compares the rotational-angle indication value θa indicated by the synchronization signal and the rotational-angle indication value θr indicated by the encoder 35, and calculates the difference Δθ (the angular difference Δθ) therebetween. The angular difference Δθ is input to the velocity-command computing unit 62. The velocity-command computing unit 62 performs predetermined computation based on the angular difference Δθ, and calculates a command value ωa of an angular velocity (rotational velocity); the command value ωa is transmitted to the velocity comparing unit 63. Then, the velocity comparing unit 63 compares the angular-velocity command value ωa and an angular velocity actual value ωr transmitted from the encoder 35 of the rotating drum 22, calculating a difference Δω (angular velocity difference Δω) therebetween. The angular velocity difference Δω is transmitted to the drive-current computing unit 64. The drive-current computing unit 64 performs predetermined computation based on the angular velocity difference Δω, and obtains a drive current I that reduces the angular velocity difference Δω. The obtained drive current I is supplied to the motor 30, and drives the motor 30.

Here, the rotational motion of the rotating drum 22 is transmitted to the encoder 35 using an appropriate rotational-movement transmission mechanism as shown in FIG. 5. A detailed description thereof will be given later; in this example, a so-called endless belt power transmission device having pulleys 21p, 42p, 42p, and 35p and timing belts 37 and 38 is used. Furthermore, adjusting a rotation ratio R of the input shaft 35a of the encoder 35 to the rotating drum 22, that is, adjusting devices so that the input shaft 35a rotates once during a period in which the rotating drum 22 rotates by the rotational angle θP corresponding to the arrangement pitch P, is performed by adjusting the ratio between the diameter (the diameter of a pitch circle) of the pulley 21p on the rotational shaft 21 of the rotating drum 22 and the diameter (the diameter of a pitch circle) of the pulley 35p on the input shaft 35a, for example.

<<<Change in Product Size in Fiber Depositing Apparatus 20>>>

In the production line 10, the size of the napkins 1 that are to be produced is changed periodically. Accordingly, change in product size is performed also in the fiber depositing apparatus 20. Furthermore, at the time of size change, the production pitch P in the transport direction, the length of the absorbent bodies 3, and the like change. Thus, in the rotating drum 22, the arrangement pitch P of the molds 23, the length of the molds 23, and the like are changed. The following is a description concerning an exemplary case of change in product size from M to L.

Change in product size in the rotating drum 22 is performed, for example, by detaching the mold plates 29M for the M size from the drum main body 25 of the rotating drum 22 in FIG. 4 and, in their place, attaching the mold plates 29L for the L size (not shown). At that time, benchmarks (or keys and key grooves) that are formed on the drum main body 25 serve as the reference points for predetermined positions, and the mold plates 29L are attached to the positions. The positions are positions where the positional relationship necessary for synchronization with the cutter roll 71 is ensured through adjustment performed in advance. Thus, if the mold plates 29L are attached to the positions, the positional relationship necessary for synchronization between the rotating drum 22 and the cutter roll 71 is ensured.

Furthermore, as a result of the replacement to the mold plates 29L for the L size, a number N of molds 23 that are formed on the rotating drum 22 is changed, for example, from 6 to 5. Moreover, due to the replacement, the arrangement pitch P of the molds 23 in the rotating direction Dc on the rotating drum 22 is also changed from an arrangement pitch PM for the M size to an arrangement pitch PL for the L size. In this example, the arrangement pitch PL is 1.2 times (=6/5) as large as the arrangement pitch PM.

On the other hand, the drum main body 25 provided with the rotational shaft 21 and the motor 30 used as a driving source for driving the drum main body 25 are not replaced, and they are used for both sizes. Since only the mold plates 29 (29M→29L) are replaced, the outer diameter of the rotating drum 22 does not substantially change at the time of change in product size from M to L. Thus, the scattering duct 51 that is disposed opposite the rotating drum 22 is used without change.

Moreover, also regarding the synchronization signal, the corresponding relationship that a signal indicating a phase of 0° to 360° is repeatedly output during a period when the semi-finished products are conveyed by the production pitch P is maintained regardless of change in product size from M to L. That is to say, in the synchronization signal, a phase range of 0° to 360° is allocated to the production pitch PM for the M size; in a similar manner, a phase range of 0° to 360° is allocated to the production pitch PL for the L size (=1.2×PM) and the synchronization signal is output.

The reason that corresponding relationship is maintained in this manner is as follows. At the time of change in product size, the absorbent-body rotary cutter 70 that is to generate the synchronization signal is also replaced from the cutter roll 71 for the M size to the cutter roll 71 for the L size. Therefore, the relationship that the cutter roll 71 rotates once during a period between cuttings of the semi-finished product 1a at the production pitch PL for the L size is maintained.

However, according to the above-described change in product size, the corresponding relationship between the arrangement pitch P of the molds 23 and the detection signal from the encoder 35 changes.

Specifically, as shown in FIG. 5, before change in product size, the input shaft 35a of the encoder 35 rotates once during a period when the rotating drum 22 rotates by a rotational angle θPM (60° (=360°/6)) which corresponds to the arrangement pitch PM for the M size. Thus, during a period when the rotating drum 22 rotates by a rotational angle θPL (72° (=360°/5)) which corresponds to the arrangement pitch PL for the L size, the input shaft 35a of the encoder 35 rotates more than once. Specifically, the input shaft 35a rotates 1.2 times. As a result, the encoder 35 outputs a signal exceeding a phase range of 0° to 360°.

Accordingly, at the time of change in product size to L, the setting has to be changed such that the input shaft 35a of the encoder 35 rotates once during a period when the rotating drum 22 rotates by the rotational angle θPL which corresponds to the arrangement pitch PL for the L size. As described in "Technical Problem" above, this change is performed by replacing the pulley 35p of the encoder 35. This replacement operation requires an inordinate amount of effort. Furthermore, it is possible that the relative rotation between the rotational shaft 21 of the rotating drum 22 and the input shaft 35a of the encoder 35 occur at the time of replacement operation, resulting in errors in synchronization between the rotating drum 22 and the absorbent-body rotary cutter 70.

Figure 7:
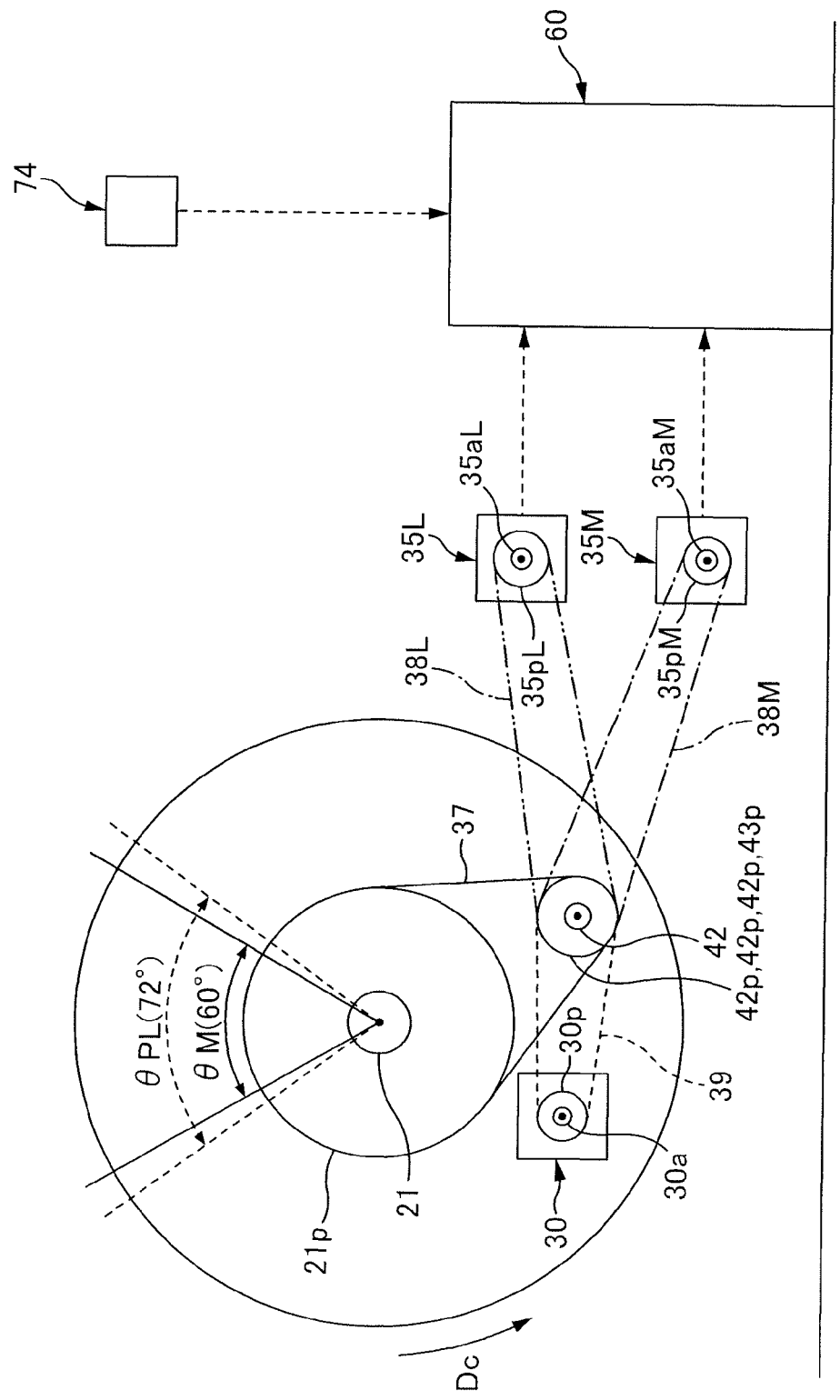
FIG. 7 is a schematic side view of the rotating drum 22 according to this embodiment viewed from the side of the driving mechanism.

In this embodiment, the encoder 35 according to the reference example (FIG. 5) is taken as an encoder 35M for the M size, and an encoder 35L for the L size is additionally provided. That is to say, the encoders 35M and 35L respectively dedicated to the M size and the L size are arranged (FIG. 7). The encoders 35M and 35L that are to be used are selectively switched according to the size of products that are to be produced. This makes it unnecessary to adjust the encoders 35M and 35L at the time of change in product size, which results in reducing the work load at the time of change in product size. Hereinafter, this configuration will be described in detail.

FIG. 7 is a schematic side view of the rotating drum 22 according to this embodiment viewed from the side of the driving mechanism.

As shown in FIG. 7, the encoder 35M for the M size (corresponding to a "first signal-generating section") and the encoder 35L for the L size (corresponding to a "second signal-generating section") are arranged near the rotating drum 22. The encoders 35M and 35L have the same specification, and respectively have input shafts 35aM and 35aL. To each of the input shafts 35aM and 35aL, a rotational motion is input from the rotational shaft 21 of the rotating drum 22 via an endless belt power transmission mechanism which serves as an exemplary rotational-movement transmission mechanism. The rotational motion is input at predetermined rotation ratios RM and RL respectively to the input shafts 35aM and 35aL.

Here, the rotation ratio RM of the input shaft 35aM (corresponding to a "first input shaft") of the encoder 35M for the M size with respect to the rotational shaft 21 of the rotating drum 22 is set to 6 (=6/1) because a number NM of molds 23 on the rotating drum 22 is 6. The rotation ratio RL of the input shaft 35aL (corresponding to a "second input shaft") of the encoder 35L for the L size is set to 5 (=5/1) because a number NL of molds 23 is 5.

Accordingly, in the encoder 35M for the M size, the input shaft 35aM rotates once during a period when the rotating drum 22 rotates by the rotational angle θPM (60° (=360°/6)) which corresponds to the arrangement pitch PM of the molds 23 for the M size. Therefore, the encoder 35M for the M size outputs a signal in a phase range of 0° to 360° per rotation corresponding to the arrangement pitch PM of the rotating drum 22.

Also, in the encoder 35L for the L size, the input shaft 35aL rotates once during a period when the rotating drum 22 rotates by the rotational angle θPL (72° (=360°/5)) which corresponds to the arrangement pitch PL of the molds 23 for the L size. Therefore, the encoder 35L for the L size outputs a signal in a phase range of 0° to 360° per rotation corresponding to the arrangement pitch PL of the rotating drum 22.

Thus, change in product size in the encoder 35 is completed by switching appropriate connection of signal input to the controller 60 between the encoder 35M for the M size and the encoder 35L for the L size by means such as: a selector switch realized as an electric circuit, etc outside the controller 60; and a selector switch realized by a program executable by a processor of the controller 60.

This makes it unnecessary to replace the pulley of the input shaft 35a at the time of change in product size. That is to say, at a time such as a trial performed when the fiber depositing apparatus 20 has been just constructed, the corresponding relationship between the positions of the molds 23 on the rotating drum 22 in the rotating direction Dc and signal phases of the encoders 35M and 35L are set only once for each of the L size and the M size. Thereafter, the change in product size can be made basically only by performing this switching operation.

Here, in this embodiment, an endless belt power transmission mechanism having a relay shaft 42 as shown in FIG. 7 is used as a rotational motion transmission machine that transmits the rotational motion at the rotation ratios RM and RL.

Specifically, at a certain position between the rotating drum 22 and the encoders 35M and 35L, one relay shaft 42 is disposed rotatably about its axis. Pulleys 21p, 35pM, and 35pL are respectively fixed coaxially and integrally on a predetermined portion on the rotational shaft 21 of the rotating drum 22, the input shaft 35aM of the encoder 35M for the M size, and the input shaft 35aL of the encoder 35L for the L size. Moreover, three pulleys 42p having the same diameter are fixed coaxially and integrally to the relay shaft 42.

The three pulleys 42p on the relay shaft 42 respectively correspond to the pulley 21p on the rotational shaft 21, the pulley 35pM on the input shaft 35aM, and the pulley 35pL on the input shaft 35aL. Timing belts 37, 38M, and 38L are respectively stretched between the pulleys 42p and their corresponding pulleys 21p, 35pM, and 35pL. Therefore, the rotational motion of the rotating drum 22 is input via the relay shaft 42 to the encoders 35M and 35L.

Here, the rotation ratios RM and RL are respectively determined based on the ratio between the diameter of the pulley 21p on the rotating drum 22 and the diameter of the pulley 35pM on the encoder 35M and the ratio between the diameter of the pulley 21p and the diameter of the pulley 35pL on the encoder 35L. Thus, in this embodiment, the diameter of the pulley 21p on the rotating drum 22 is taken as Dp, and the diameter of the pulley 35pM for the M size is set to ⅙×Dp. Also, the diameter of the pulley 35pL for the L size is set to ⅕×Dp.

The relay shaft 42 is used for increasing the degree of freedom in the arrangement position of the encoder 35M (35L). And the shaft 42 is also used for precisely transmitting the rotational motion of the rotating drum 22 to the input shafts 35aM and 35aL. The latter reason will be described below. If the relay shaft 42 is used, the rotation ratio RM (RL) of rotational motion transmitted from the rotational shaft 21 to the input shaft 35aM (35aL) can be divided into two rotation ratios that are each smaller than the rotation ratio RM (RL). Accordingly, the rotation ratios can be gradually converted. Furthermore, since two timing belts 37 and 38M (37 and 38L) are used, the length of each of the timing belts 37 and 38M (37 and 38L) can be shortened. Accordingly, slacks of the timing belts 37 and 38M (37 and 38L) become smaller. Therefore, a tension that is to be applied to the timing belts 37 and 38M (37 and 38L) for taking up the slacks can be reduced. This can reduce loads that act on the rotational shaft 21 and the input shaft 35aM (35aL), resulting in stabilization of the rotational motion of the shafts 21 and 35aM (35aL). This makes it possible to precisely transmit the rotational motion of the rotating drum 22 to the input shaft 35aM (35aL).

Note that, as the conditions for dividing the rotation ratio into two smaller rotation ratios, the rotation ratio of the relay shaft 42 to the rotational shaft 21 has to be larger than 1, and smaller than the rotation ratio RM (=6) for the M size or the rotation ratio RL (=5) for the L size. Accordingly, the diameter of the pulleys 42p on the relay shaft 42 has to be smaller than the diameter of the pulley 21p on the rotating drum 22, and larger than the diameters of the input shafts 35aM and 35aL.

However, the relay shaft 42 does not necessarily have to be used. That is to say, one timing belt may be wrapped directly around the pulley 21p on the rotational shaft 21 of the rotating drum 22 and the pulley 35pM (35pL) on the input shaft 35aM (35aL) of the encoder 35M (35L), to transmit the rotational motion.

In the example in FIG. 7, the motor 30 for driving to rotate the rotating drum 22 inputs the rotational driving force via the relay shaft 42 to the rotating drum 22. That is to say, another pulley 43p is integrally and coaxially disposed on the relay shaft 42, and a timing belt 39 is wrapped around the pulley 43p and a pulley 30p on a driving rotational shaft 30a of the motor 30. Accordingly, the rotational driving force is transmitted to the relay shaft 42, and is then transmitted from the relay shaft 42 to the rotating drum 22 via the timing belt 37 and the rotational shaft 21.

Note that the method for transmitting the rotational driving force of the motor 30 is not limited thereto. For example, it is unnecessary to use the relay shaft 42. That is to say, one timing belt may be wrapped directly around the pulley 21p on the rotational shaft 21 of the rotating drum 22 and the pulley 30p on the driving rotational shaft 30a of the motor 30, to transmit the rotational driving force.

Figure 8:
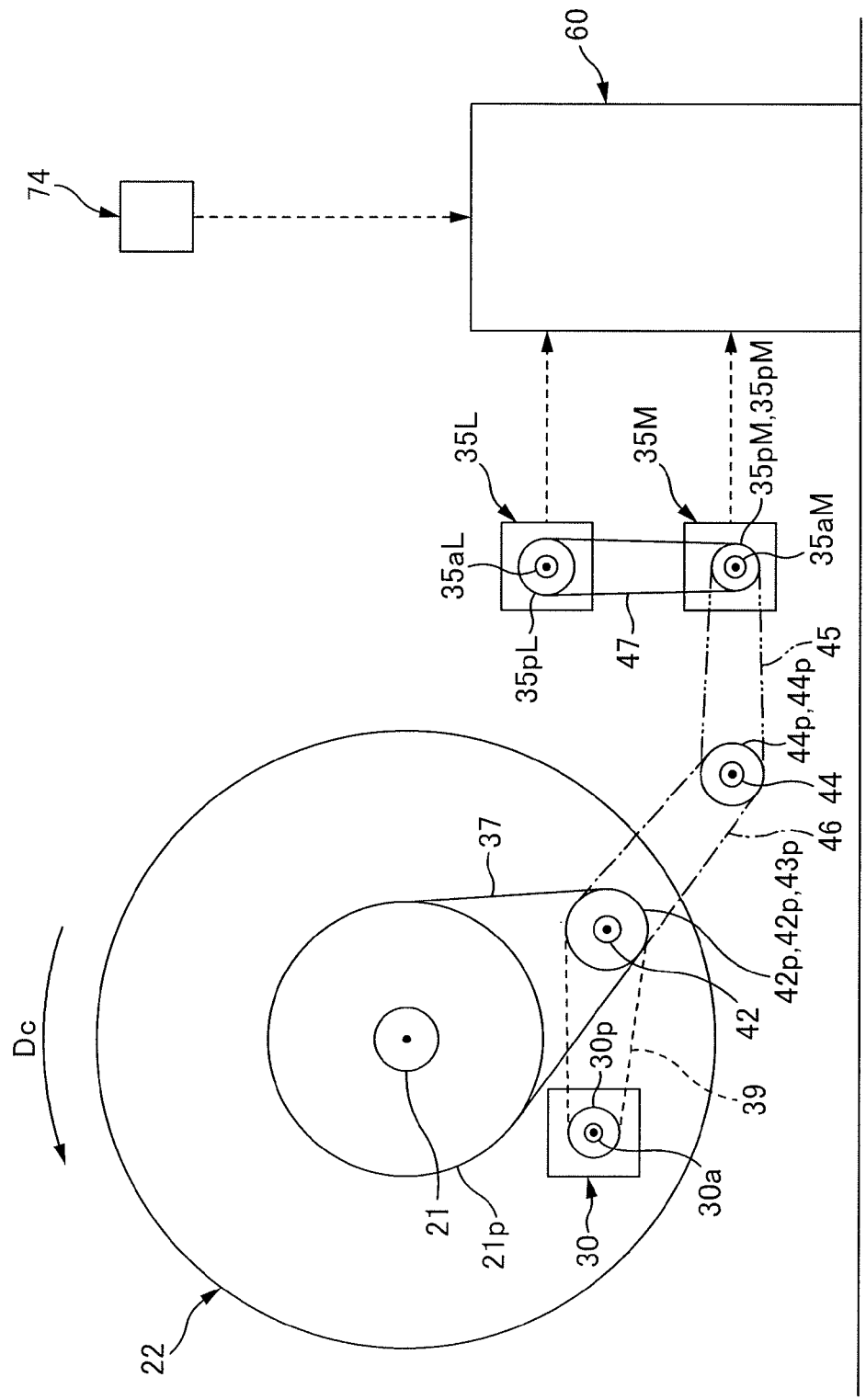
FIG. 8 is an explanatory view of another example of a timing belt wrapping pattern in a rotational-movement transmission mechanism.

FIG. 8 is an explanatory view of another example of a timing belt wrapping pattern in the rotational-movement transmission mechanism. In this example, a relay shaft is also used as in the above-described example. However, the number of relay shafts used is not one; two relay shafts 42 and 44 are used as an example of a plurality of relay shafts. Furthermore, when transmitting the rotational motion of the rotating drum 22 to the encoder 35L for the L size, the input shaft 35aM of the encoder 35M for the M size is also used as a relay shaft.

Specifically, the first relay shaft 42 and the second relay shaft 44 are arranged at certain positions between the rotational shaft 21 of the rotating drum 22 and the encoders 35M and 35L so as to be spaced apart from each other. The first relay shaft 42 is located closer to the rotational shaft 21 of the rotating drum 22, and has integrally and coaxially a pair of pulleys 42p and 42p having the same diameter. The second relay shaft 44 is located closer to the encoders 35M and 35L, and has integrally and coaxially a pair of pulleys 44p and 44p having the same diameter. One of the pulleys 42p and 42p on the first relay shaft 42 is connected via the timing belt 37 to the pulley 21p on the rotational shaft 21 of the rotating drum 22. The other pulley 42p is connected via a timing belt 46 to one of the pulleys 44p of the second relay shaft 44. The other pulley 44p on the second relay shaft 44 is connected via a timing belt 45 to the pulley 35pM on the input shaft 35aM of the encoder 35M for the M size. Accordingly, the rotational motion of the rotating drum 22 is input to the encoder 35M for the M size via the first relay shaft 42 and the second relay shaft 44.

Note that the input shaft 35aM of the encoder 35M for the M size has integrally and coaxially another pulley 35pM having the diameter which is the same as the above-described pulley 35pM. This pulley 35pM is connected via a timing belt 47 to the pulley 35pL on the input shaft 35aL of the encoder 35L for the L size. Thus, the rotational motion of the rotating drum 22 is input to the encoder 35L for the L size via the input shaft 35aM of the encoder 35M for the M size.

Other Embodiments

In the description above, an embodiment of the invention was described, but the invention is not limited to this embodiment, and modifications such as those disclosed below are possible.

In the foregoing embodiment, the pulp fiber 5 is given as an example of the main material of the absorbent-body material. However, the invention is not limited thereto. As the main material, a superabsorbent polymer may also be used. Note that the "main material" herein refers to the material that is contained in the largest amount in the absorbent body 3 in terms of weight percentage (or volume percentage).

In the foregoing embodiment, the change in product size between the M size and the L size is given as an example. However, change in product size is not limited thereto. The concept of the foregoing embodiment may be applied to change in product size among three sizes consisting of S, M, and L, or among four sizes consisting of these three sizes and LL. If the concept is applied to change in product size among three sizes, an encoder 35S dedicated to the S size is additionally provided in the configuration of the foregoing embodiment. As a result, the rotating drum 22 includes three encoders in total: the encoder 35S, 35M, and 35L.

In the foregoing embodiment, the endless belt power transmission mechanism having the pulleys 21p, 42p, 35pM, and 35pL and the timing belts 37, 38M, and 38L is described as an example of a rotational-movement transmission mechanism. However, the invention is not limited thereto as long as the rotational motion can be transmitted. For example, a gear train having a plurality of gears which mesh with each other may be used.

In the foregoing embodiment, the change in product size in the rotating drum 22 is performed by merely replacing the mold plates 29 in FIG. 4, and the drum main body 25 is not replaced. However, in some cases, change in product size in the rotating drum 22 may be performed by replacing the drum main body 25 to which the mold plates 29 are attached.

In this case, the rotational shaft 21 of the rotating drum 22 includes, for example, a rotational shaft portion on the rotating drum 22 side and a rotational shaft portion on the motor 30 side, these portions being coupled separably. Examples of the separable coupling structure include an appropriate shaft coupling. The rotational shaft portion on the motor 30 side is rotatably supported via a bearing member on the base of the fiber depositing apparatus 20. Furthermore, on the rotational shaft portion (corresponding to a "predetermined portion") on the motor 30 side, the pulley 21p that transmits the rotational motion to the encoders 35M and 35L is disposed.

At the time of change in product size, the rotating drum 22 is detached at the coupling structure and removed from the production line 10. Subsequently, the rotating drum 22 is replaced with one for the size of napkins 1 that are to be produced next; the rotational shaft portion on the rotating drum 22 side is coupled to the rotational shaft portion on the motor 30 side which remains in the production line 10. This coupling is made with reference to benchmarks, key members, and the like provided on these rotational shaft portions. Accordingly, the corresponding relationship between the positions of the molds 23 on the rotating drum 22 in the rotating direction Dc and the rotational-angle indication values θr indicated by the encoders 35M and 35L is kept at a predetermined relationship necessary for the synchronization operation; on the rotating drum 22 in the rotating direction Dc means the rotational positions on the rotating drum 22. In this example, the rotating drum 22 for the M size corresponds to a "first-pitch positioning member", and the rotating drum 22 for the L size corresponds to a "second-pitch positioning member".

Moreover, in some cases, change in product size in the rotating drum 22 may be performed by replacing the cylindrical section 26 to which the mold plates 29 have been attached. In that case, the coupling section between the spoke-like members 28 and the cylindrical section 26 in the drum main body 25 is configured in advance as a separable coupling structure such as bolting.

At the time of change in product size, the cylindrical section 26 is detached at the coupling section and removed from the production line 10. That is to say, the spoke-like members 28 and the rotational shaft 21 remain in the production line 10 in the state before detaching the cylindrical section 26. Subsequently, the cylindrical section 26 is replaced with one which is for the size of napkins 1 that are to be produced next and to which the mold plates 29 are attached; the cylindrical section 26 is coupled to the spoke-like members 28 which remain in the production line 10. This coupling is made with reference to reference points such as benchmarks provided on the cylindrical section 26 and the spoke-like members 28. Accordingly, the corresponding relationship between the positions of the molds 23 on the rotating drum 22 in the rotating direction Dc and the rotational-angle indication values θr indicated by the encoders 35M and 35L is kept at a relationship necessary for the synchronization operation; the positions of the molds 23 on the rotating drum 22 in the rotating direction Dc means rotational positions on the rotating drum 22. In this example, the cylindrical section 26 for the M size to which the mold plates 29 are attached corresponds to a "first-pitch positioning member", and the cylindrical section 26 for the L size to which the mold plates 29 are attached corresponds to a "second-pitch positioning member".

In the foregoing embodiment, the rotational driving of the rotating drum 22 is synchronized with the cutting operation by the absorbent-body rotary cutter 70. However, the invention is not limited thereto. For example, instead of the cutter 70, the rotational driving of the rotating drum 22 may be synchronized with the embossment pressing apparatus 80 or the rotary die cutter apparatus 90. In these cases, it goes without saying that a synchronization signal is output from an encoder that detects the operation of the apparatus 80 or 90.

The rotational driving of the embossment pressing apparatus 80 or the rotary die cutter apparatus 90 as another apparatus also may be synchronized based on the synchronization signal of the cutter 70.

The transport mechanisms 12 also may be controlled so as to perform the transport operation in synchronization with the cutter 70, or may be controlled so as to have the transport velocity which is the same as the circumferential velocity of the flat blade 71c on the cutter 70.

In the foregoing embodiment, the encoder 35M is given as an example of the first signal-generating section, and the signal indicating a phase of 0° to 360° is given as an example of the first rotational-angle signal. However, the invention is not limited thereto. It is sufficient that the signal has the same specification as the synchronization signal and the signal is repeatedly generated taking the rotational angle θPM of the rotating drum 22 as a unit, the rotational angle θPM corresponding to the arrangement pitch PM which is the first pitch.

For example, the first rotational-angle signal may be a signal including 8192 digital values from 0 to 8191 which are uniformly allocated to the rotational angle θPM of the rotating drum 22, or may be a signal including a certain number of pulses that are uniformly allocated to the rotational angle θPM.

In the foregoing embodiment, the encoder 35L is given as an example of the second signal-generating section, and the signal indicating a phase of 0° to 360° is given as an example of the second rotational-angle signal. However, the invention is not limited thereto. It is sufficient that the signal has the same specification as the synchronization signal and the signal is repeatedly generated taking the rotational angle θPL of the rotating drum 22 as a unit, the rotational angle θPL corresponding to the arrangement pitch PL which is the second pitch.

For example, the second rotational-angle signal may be a signal including 8192 digital values from 0 to 8191 which are uniformly allocated to the rotational angle θPL of the rotating drum 22, or may be a signal including a certain number of pulses that are uniformly allocated to the rotational angle θPL.

In the foregoing embodiment, the encoder 74 is given as an example of the unit that generates a synchronization signal, and the signal indicating a phase of 0° to 360° is given as an example of the synchronization signal. However, the invention is not limited thereto. It is sufficient that the signal is repeatedly generated taking the unit amount of motion of another apparatus as a unit, the unit amount of motion corresponding to the production pitch P.

For example, the synchronization signal may be a signal including 8192 digital values from 0 to 8191 which are uniformly allocated to the rotational angle corresponding to one rotation of the cutter roll 71, which is a unit amount of motion of the cutter roll 71, or may be a signal including a certain number of pulses that are uniformly allocated to the rotational angle.

LIST OF REFERENCE NUMERALS 1 sanitary napkin (absorbent article),
1a semi-finished product, 1b semi-finished product, 1c semi-finished product, 1d semi-finished product, 1e semi-finished product,
2 top sheet, 2r sheet roll,
3 absorbent body,
4 back sheet, 4r sheet roll,
5 pulp fiber (absorbent-body material), 5a mixed air,
6 carrier sheet, 6r sheet roll,
7 embossed groove,
10 production line, 12 suction belt conveyor (transport mechanism),
15 reel,
20 fiber stacking apparatus (absorbent-body manufacturing apparatus),
21 rotational shaft, 21p pulley,
22 rotating drum (drum), 22a outer circumferential face,
23 mold (recess sections), 24 air permeable member, 24h air hole,
25 drum main body,
26 cylindrical section, 26a outer circumferential face, 26e two end edges,
26h opening section,
27 circular fixing wall,
28 spoke-like member,
29 mold plate,
29M mold plate (first-pitch positioning member),
29L mold plate (second-pitch positioning member),
29a arc-shaped plate, 29h opening section,
30 motor (driving source), 30a driving rotational shaft, 30p pulley,
35 rotary encoder,
35M rotary encoder (first signal-generating section),
35L rotary encoder (second signal-generating section),
35a input shaft, 35aM input shaft, 35aL input shaft,
35p pulley, 35pM pulley, 35pL pulley,
37 timing belt,
38 timing belt,
38M timing belt, 38L timing belt, 39 timing belt,
42 relay shaft, 42p pulley, 43p pulley,
44 relay shaft, 44p pulley,
45 timing belt, 46 timing belt, 47 timing belt,
51 scattering duct (duct), 51a scattering opening,
53 suction duct,
60 controller, 61 position comparing unit, 62 velocity-command computing unit,
63 velocity comparing unit, 64 drive-current computing unit,
70 absorbent-body rotary cutter, 71 cutter roll, 71a outer circumferential face,
71c flat blade, 72 anvil roll,
74 rotary encoder,
80 embossment pressing apparatus, 81 embossing roll, 82 anvil roll,
85 HMA application apparatus,
90 rotary die cutter apparatus, 91 cutter roll, 92 anvil roll,
Z1 first zone, Z2 second zone, S substantially closed space

The invention claimed is:

1. An absorbent-body manufacturing apparatus that has a driving source that drives a drum to rotate about a rotational shaft in synchronization with another apparatus based on a synchronization signal, the synchronization signal being repeatedly output taking a unit amount of motion of the other apparatus as a unit, the unit amount of motion corresponding to a production pitch,
that manufactures an absorbent body by supplying an absorbent-body material and depositing the absorbent-body material in a plurality of recess sections,
the supplying being performed from a duct toward the plurality of recess sections,
the plurality of recess sections being spaced at a predetermined arrangement pitch in a rotating direction on an outer circumferential face of the drum,
the duct being disposed at a predetermined position in the rotating direction, comprising:
a first-pitch positioning member for setting the arrangement pitch to a first pitch;
a second-pitch positioning member for setting the arrangement pitch to a second pitch that is different from the first pitch;
a first signal-generating section that repeatedly generates a first rotational-angle signal based on a rotation of the drum taking a rotational angle of the drum as a unit, the rotational angle of the drum corresponding to the first pitch;
a second signal-generating section that repeatedly generates a second rotational-angle signal based on a rotation of the drum taking a rotational angle of the drum as a unit, the rotational angle of the drum corresponding to the second pitch; and
a controller that controls rotational driving of the driving source, wherein
in the case where the arrangement pitch is set to the first pitch,
the controller controls rotational driving of the driving source based on the first rotational-angle signal and the synchronization signal, and
in the case where the arrangement pitch is set to the second pitch,
the controller controls rotational driving of the driving source based on the second rotational-angle signal and the synchronization signal.

2. An absorbent-body manufacturing apparatus according to claim 1, wherein
the first rotational-angle signal and the second rotational-angle signal are signals each having the same specification as the synchronization signal.

3. An absorbent-body manufacturing apparatus according to claim 2, wherein
the first rotational-angle signal is a signal indicating a phase of 0° to 360°,
the second rotational-angle signal is a signal indicating a phase of 0° to 360°, and
the synchronization signal is a signal indicating a phase of 0° to 360°.

4. An absorbent-body manufacturing apparatus according to claim 1, wherein
the first signal-generating section and the second signal-generating section are signal-generating sections having the same specification,
the first signal-generating section
has a first input shaft, and
generates the first rotational-angle signal by rotation of the first input shaft,
the second signal-generating section
has a second input shaft, and
generates the second rotational-angle signal by rotation of the second input shaft,
the rotational shaft of the drum integrally rotates with the drum,
a rotational motion of the drum is input from the rotational shaft to the first input shaft and the second input shaft via a rotational-movement transmission mechanism, and
when the number of the recess sections arranged at the first pitch PM on the drum is NM, and the number of the recess sections arranged at the second pitch PL on the drum is NL,
the rotational-movement transmission mechanism is set such that a rotation ratio RM of the first input shaft to the rotational shaft is NM and such that a rotation ratio RL of the second input shaft to the rotational shaft is NL.

5. An absorbent-body manufacturing apparatus according to claim 4, wherein
the rotational-movement transmission mechanism has at least one relay shaft,
the rotational motion of the drum is transmitted from the rotational shaft to the first input shaft and the second input shaft via the relay shaft,
the rotation ratio RM is divided by the relay shaft into a plurality of rotation ratios that are each smaller than the rotation ratio RM, and
the rotation ratio RL is divided by the relay shaft into a plurality of rotation ratios that are each smaller than the rotation ratio RL.

6. An absorbent-body manufacturing apparatus according to claim 4, wherein
in order to transmit the rotational motion of the drum to the first input shaft and the second input shaft, the rotational shaft is coupled to the rotational-movement transmission mechanism at a predetermined portion on the rotational shaft, and
the predetermined portion is commonly applied to both the case where the arrangement pitch is the first pitch and the case where the arrangement pitch is the second pitch.

7. An absorbent-body manufacturing apparatus according to claim 1, wherein
an ejection opening of the duct for ejecting and supplying the absorbent-body material is disposed opposite the outer circumferential face of the drum, and
a diameter of the drum formed by the first-pitch positioning member is equal to a diameter of the drum formed by the second-pitch positioning member.

* * * * *